(12) United States Patent
Rekoske et al.

(10) Patent No.: US 8,022,263 B2
(45) Date of Patent: Sep. 20, 2011

(54) SELECTIVE AROMATICS ISOMERIZATION PROCESS

(75) Inventors: James E. Rekoske, Glenview, IL (US); Patrick C. Whitchurch, Bossier City, LA (US); Robert B. Larson, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 479 days.

(21) Appl. No.: 12/274,007

(22) Filed: Nov. 19, 2008

(65) Prior Publication Data

US 2010/0125160 A1    May 20, 2010

(51) Int. Cl.
*C07C 5/22*    (2006.01)
(52) U.S. Cl. ........................................ 585/481; 585/482
(58) Field of Classification Search .................. 585/481, 585/482
See application file for complete search history.

(56) References Cited

U.S. PATENT DOCUMENTS

| 4,159,282 | A  | 6/1979  | Olson et al. ................... 585/481 |
| 4,899,011 | A  | 2/1990  | Chu et al. ...................... 585/481 |
| 5,689,027 | A  | 11/1997 | Abichandani et al. ........ 585/481 |
| 6,051,744 | A  | 4/2000  | Nacamuli et al. ............. 585/481 |
| 6,143,941 | A  | 11/2000 | Sharma et al. ................ 585/481 |
| 6,355,853 | B1 | 3/2002  | Sharma et al. ................ 585/481 |
| 7,115,538 | B2 | 10/2006 | Buchanan et al. .............. 502/60 |

FOREIGN PATENT DOCUMENTS

| EP | 0909266 B1 | 3/1998  |
| EP | 1056695 B1 | 11/1999 |

*Primary Examiner* — Thuan Dinh Dang
(74) *Attorney, Agent, or Firm* — Maryann Maas

(57) ABSTRACT

This invention is drawn to a process for isomerizing a non-equilibrium mixture of xylenes and ethylbenzene using a catalyst comprising a zeolite having specific particle-size characteristics, a platinum-group metal and a silica binder. A relatively minimal amount of hydrogen is supplied to the process on a once-through basis, resulting in low saturation of aromatics while achieving effective xylene isomerization with reduced processing costs.

2 Claims, 2 Drawing Sheets

SELECTIVE AROMATICS ISOMERIZATION PROCESS

FIELD OF THE INVENTION

This invention relates to catalytic hydrocarbon conversion, and more specifically to aromatics isomerization.

GENERAL BACKGROUND AND RELATED ART

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20-25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture which approaches equilibrium concentrations.

Various processes and catalysts have been developed to isomerize $C_8$ aromatics. In selecting appropriate technology, it is desirable to operate the isomerization process as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e. very close approach to equilibrium) and high utility costs due to the large recycle rate of unconverted $C_8$ aromatics.

Processes for isomerization of $C_8$ aromatics ordinarily are classified by the manner of converting ethylbenzene associated with the xylene isomers. Ethylbenzene is not easily isomerized to xylenes, but it normally is converted in the isomerization unit because separation from the xylenes by superfractionation or adsorption is very expensive. One approach is to react the ethylbenzene to form a xylene mixture via conversion to and reconversion from naphthenes in the presence of a solid acid catalyst with a hydrogenation-dehydrogenation function. An alternative widely used approach is to dealkylate ethylbenzene to form principally benzene while isomerizing xylenes to a near-equilibrium mixture. The former approach enhances xylene yield by forming xylenes from ethylbenzene, while the latter approach commonly results in higher ethylbenzene conversion, thus lowering the quantity of recycle to the para-xylene recovery unit and concomitant processing costs.

Hydrogen generally is present in the isomerization process reactants to aid in the reaction and maintain catalyst stability. Although xylenes may be isomerized in the absence of hydrogen under some circumstances, ethylbenzene conversion generally requires the presence of hydrogen. Circulating a substantial quantity of hydrogen in an isomerization process is costly in terms of the investment and operating cost of a recycle-gas compressor and purging of valuable hydrogen from the recycle to maintain hydrogen purity. Further, high hydrogen partial pressures can result in the saturation and loss of valuable aromatics. Known art disclosing low hydrogen partial pressures for isomerization also specifies that zeolites used in such catalysts should have very small crystal sizes.

SUMMARY OF THE INVENTION

A principal object of the present invention is to provide a novel process for the isomerization of alkylaromatic hydrocarbons. More specifically, this invention is directed to the processing of $C_8$ aromatics to increase the concentration of a desired xylene isomer with reduced aromatic losses and lowered processing costs.

This invention is based on the discovery that xylene isomerization and ethylbenzene conversion can be effected with a catalyst comprising a zeolite having specific crystal-size characteristics at low ratios of hydrogen on a once-through basis to achieve reduced saturation of aromatics and elimination of compression costs.

Accordingly, one embodiment of the invention is a process for the isomerization of a non-equilibrium $C_8$-aromatic feedstock comprising contacting the feedstock with a catalyst comprising a zeolitic aluminosilicate having a median particle size greater than 1 micron, a metal component, and an inorganic oxide binder in an isomerization zone at isomerization conditions comprising a temperature of from about 320° C. to 500° C., a pressure of from 100 kPa to 5 MPa, and a mass hourly space velocity of from about 5 to 50 $hr^{-1}$ in the presence of a critical added amount of hydrogen on a once-through basis in a molar ratio relative to the feedstock of from about 0.05 to 0.4 to obtain an isomerized product comprising a higher proportion of para-xylene than in the feedstock.

A more specific embodiment is a process for the isomerization of a non-equilibrium $C_8$-aromatic feedstock comprising contacting the feedstock with a catalyst comprising an MFI zeolitic aluminosilicate having a median particle size greater than 1 micron, a platinum-group metal component, and a silica binder in an isomerization zone at isomerization conditions comprising a temperature of from about 320° C. to 500° C., a pressure of from 100 kPa to 5 MPa, and a mass hourly space velocity of from about 5 to 50 $hr^{-1}$ in the presence of a critical added amount of hydrogen on a once-through basis in a molar ratio relative to the feedstock of from about 0.05 to 0.4 to obtain an isomerized product comprising a higher proportion of para-xylene than in the feedstock.

A yet more specific embodiment is a process for the isomerization of a non-equilibrium $C_8$-aromatic feedstock comprising contacting the feedstock with a catalyst comprising from about 10 to 99 mass-% of an MFI zeolitic aluminosilicate having a pore diameter of from 5 to 8 angstroms and a median particle size greater than 1 micron, from about 200 to 800 mass-ppm on an elemental basis of a platinum-group metal component, and the balance of a silica binder, wherein the catalyst has a 4.6 torr water capacity between 3 to 5 mass-%, in an isomerization zone at isomerization conditions comprising a temperature of from about 320° C. to 500° C., a pressure of from 100 kPa to 5 MPa, and a mass hourly space velocity of from about 5 to 50 $hr^{-1}$ in the presence of a critical added amount hydrogen on a once-through basis in a molar ratio relative to the feedstock of from about 0.05 to 0.4 to obtain an isomerized product comprising a higher proportion of para-xylene than in the feedstock.

Other specific embodiments will become clear from the following detailed description of the invention.

DETAILED DESCRIPTION OF THE INVENTION

Figure 1:
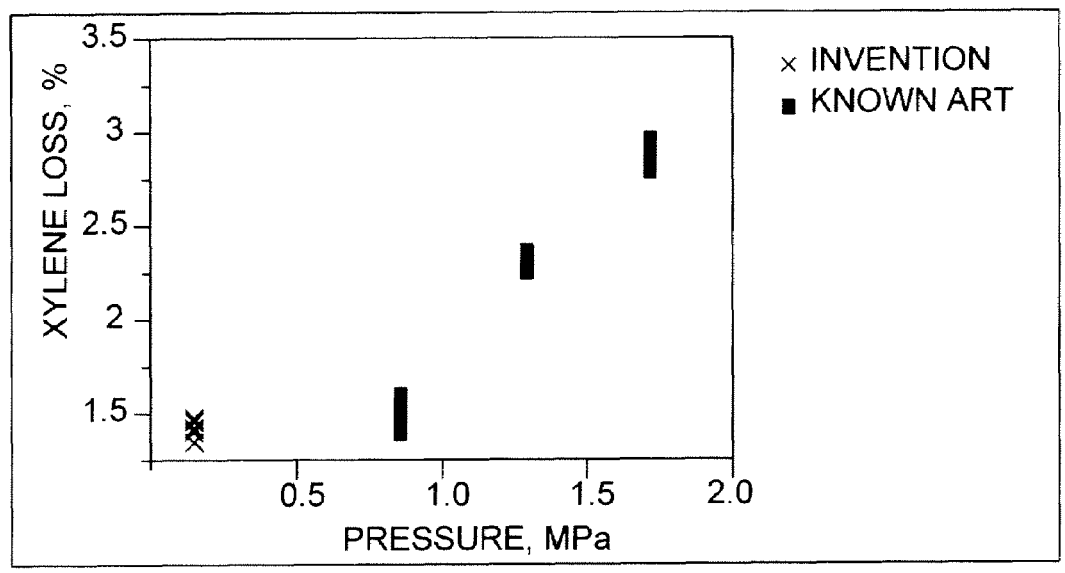
FIG. 1 compares xylene losses for the process of the invention compared to a process of the known art.

The feedstock to aromatics isomerization comprises isomerizable alkylaromatic hydrocarbons of the general formula $C_nH_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example but without so limiting the invention, ortho-xylene, meta-xylene, para-xylene, ethylbenzene, ethyltoluenes, trimethylbenzenes, propylbenzenes, ethyldimethylbenzenes, diethylbenzenes, methylpropylbenzenes, ethylpropylbenzenes, triethylbenzenes, di-isopropyl-benzenes, and mixtures thereof.

Isomerization of a $C_8$-aromatic feedstock containing ethylbenzene and xylenes is a particularly preferred application of the invention. Generally such a mixture will have an ethylbenzene content in the approximate range of 1 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_8$-aromatic isomer is present in a concentration that differs substantially from the equilibrium concentration at isomerization conditions. Usually the nonequilibrium mixture is prepared by removal of para- and/or ortho-xylene from a fresh $C_8$-aromatics feed obtained from processes, such as catalytic reforming and/or extraction, for the production and recovery of aromatics from other hydrocarbons.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feedstock, preferably in admixture with a critical added amount of hydrogen, is contacted with a catalyst of the type hereinafter described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feedstock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone.

The reactants may be contacted with the catalyst bed in upward-, downward-, or radial-flow fashion, and the reactants may be in the liquid phase, a mixed liquid-vapor phase, or a vapor phase when contacted with the catalyst.

The alkylaromatic feedstock, preferably a non-equilibrium mixture of $C_8$ aromatics, is contacted with the isomerization catalyst at suitable alkylaromatic-isomerization conditions. Such conditions comprise a temperature ranging from about 100° to 600° C. or more, and preferably is in the range of from about 320° to 500° C. The pressure generally is from about 100 kPa to 10 MPa, more usually no more than about 5 MPa, and often less than about 500 kPa. Sufficient catalyst is contained in the isomerization zone to provide a mass hourly space velocity with respect to the hydrocarbon feedstock of from about 0.5 to 100 $hr^{-1}$, and preferably 2 to 50 $hr^{-1}$; favorable results have been obtained at mass hourly space velocities of about 5 $hr^{-1}$ and higher.

The $C_8$-aromatic feedstock suitably is combined with a critical added amount of hydrogen prior to contacting the catalyst on a once-through basis, i.e. hydrogen separated from the liquid product is not recycled to the process but is sent from the process to fuel gas or other uses outside the process. Supplying a critical amount of hydrogen which is just sufficient to aid in the reaction and provide catalyst stability minimizes loss through saturation of valuable aromatics and avoids investment and operating costs associated with a recycle-gas compressor. The critical added amount of hydrogen is in a molar ratio relative to the feedstock of about 0.05 to 0.4. Preferably the ratio of added hydrogen is from about 0.05 to 0.2, and especially from about 0.05 to 0.1. Inert diluents such as nitrogen, argon and light hydrocarbons may be present in the hydrogen stream.

The particular scheme employed to recover an isomerized product from the effluent of the reactors of the isomerization zone is not deemed to be critical to the instant invention, and any effective recovery scheme known in the art may be used. Typically, the reactor effluent is condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product, alone or in combination with the fresh $C_8$ aromatics feed, by selective fractionation. The product from isomerization of $C_8$ aromatics usually is processed to selectively recover the para-xylene isomer, optionally by crystallization, alone or in combination with the fresh $C_8$ aromatics feed. Selective adsorption is preferred using crystalline aluminosilicates according to U.S. Pat. No. 3,201,491. Improvements and alternatives within the preferred adsorption recovery process are described in U.S. Pat. Nos. 3,626,020; 3,696,107; 4,039,599; 4,184,943; 4,381,419 and 4,402,832; incorporated herein by reference thereto.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone from which pure para-xylene is recovered. The para-xylene-depleted stream from the separation zone, comprising a non-equilibrium mixture of $C_8$ aromatics, comprising xylenes and ethylbenzene, is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, preferably prior to para-xylene separation.

A preferred isomerization catalyst for use in the present invention comprises a molecular sieve and a refractory inorganic oxide. The preferred molecular sieves are zeolitic alumino-silicates selected from those which have a $Si:Al_2$ ratio greater than about 10, preferably greater than 20, and a pore diameter of about 5 to 8 Angstroms ( ). Specific examples of suitable zeolites are the MFI, MEL, EUO, FER, MFS, MTT, MTW, TON, MOR and FAU types of zeolites. Pentasil zeolites MFI, MEL, MTW and TON are preferred, and MFI-type zeolites, often designated ZSM-5, are especially preferred.

The preparation of the preferred MFI-type zeolites by crystallizing a mixture comprising an alumina source, a silica source and an alkali metal source is well known in the art. Conversion of an alkali-metal-form zeolite to the hydrogen form may be performed by treatment with an aqueous solution of a mineral acid or by ion exchange with ammonium salts such as ammonium hydroxide or ammonium nitrate. The molecular sieve product is formed in solution and can be recovered by standard means, such as by centrifugation or filtration and can also be washed.

The wet sieves optionally are dried and then rewetted, e.g., to achieve a slurry containing about 40 to 45 percent solids. The wet or rewetted sieves generally are flowed to a wet miller, preferably a stirred-media mill, and milled with a severity to achieve a particle-size distribution of the invention. Alternatively, dried sieves can be milled using techniques such as fluid-energy milling or ball milling and sorted using a classifier; wet milling is preferred. The median particle size of the present sieves, preferably determined by laser diffraction, is more than 1 micron, preferably at least about 1.1 micron, and more preferably between about 1.2 and 1.7 microns.

The relative proportion of zeolite in the preferred catalyst may range from about 10 to about 99 mass-%, with about 20 to about 90 mass-% being preferred. There is a tradeoff between the zeolite content of the catalyst composite and the pressure, temperature and space velocity of an isomerization operation in maintaining low xylene losses.

A refractory binder or matrix is utilized to facilitate fabrication of the isomerization catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, silica, and phosphorus-containing alumina (hereinafter referred to as aluminum phosphate). The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO—Al_2O_3$ where M is a metal having a valence of 2; which components can be added to the composite at any suitable point.

A preferred binder is a form of amorphous silica. An especially preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 300-800 $m_2/g$.

An alternative preferred binder is an alumina selected from the crystalline forms gamma-, eta-, and theta-alumina, with gamma- or eta-alumina being preferred binder components.

A preferred shape for the catalyst composite is an extrudate. The well-known extrusion method initially involves mixing of the molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pieced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

An alternative oil-drop method of preparing the catalyst composite involves the gelation of a hydrosol of the selected inorganic oxide using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours.

Yet another preferred binder or matrix component is an aluminum phosphate component. The phosphorus may be incorporated with the alumina in any acceptable manner known in the art. The zeolite and aluminum phosphate binder are mixed and formed into particles by means well known in the art such as gellation, pilling, nodulizing, marumerizing, spray drying, extrusion or any combination of these techniques. A preferred method of preparing a zeolite/aluminum phosphate support involves adding the zeolite either to an alumina sol or a phosphorus compound and forming a mixture of the alumina sol/zeolite/phosphorus mixture into particles by employing the oil-drop method or by spray-drying of the mixture. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm. calcining the spherical particles. The amount of aluminum phosphate component present (as the oxide) in the catalyst can range from about 10 to 70 mass percent and preferably from about 20 to 50 mass percent.

The preferred oil-drop method of preparing the aluminum phosphate is as described above and in U.S. Pat. No. 4,629,717 which is incorporated by reference. The technique described in the '717 patent involves the gellation of a hydrosol of alumina which contains a phosphorus compound. Preferred phosphorus compounds are phosphoric acid, phosphorous acid and ammonium phosphate. The relative amount of phosphorus and aluminum expressed in molar ratios ranges from about 10:1 to 1:100, and more typically from about 5:1 to 1:20/, respectively, on an elemental basis. The degree of crystallinity of the aluminum phosphate binder is controlled by the proportion of the phosphorus component. Material that is not in an amorphous phase generally is present as gamma-alumina; as the phosphorus content is decreased, the degree of crystallinity, therefore, is increased. The apparent bulk density of the spheres also varies with the phosphorus content, as a higher proportion of phosphorus decreases the average bulk density. Surface area also is controlled by phosphorus content: gamma-alumina oil-dropped spherical particles typically have surface areas up to about 250 $m^2/g$, while spheroidal particles of aluminum phosphate may have surface areas of up to about 450 $m^2/g$.

A metal component, comprising one or more metals selected from Group VIII (IUPAC 8-10), Group VIB (IUPAC 6), and Group VIIB (IUPAC 7) metals, is an essential component of the catalyst. One or more of the platinum-group metals, including one or more of platinum, palladium, rhodium, ruthenium, osmium, and iridium, are particularly favored components of the present catalyst. The preferred platinum-group metals are platinum and palladium, with platinum being especially preferred. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all of the platinum-group metal component exists in a reduced state. The platinum-group metal component generally comprises from about 10 to about 10,000 mass-ppm (parts per million) of the final catalyst composite, calculated on an elemental basis, with a level of about 100 to about 2000 mass-ppm being particularly suitable. When using a platinum component, very low levels of about 200 to 800 mass-ppm of platinum on the catalyst, on an elemental basis, are favored; levels of less than about 600 mass-ppm are especially favored and levels of about 300 to about 500 mass-ppm show excellent results. When using a palladium component, levels of about 400 to 2000 mass-ppm of palladium on the catalyst, on an elemental basis, are favored and levels of between about 500 and 1200 mass-ppm.

It is within the scope of the present invention that the catalyst may contain other metal components known to modify the effect of the platinum-group metal component. Such metal modifiers may include without so limiting the invention rhenium, tin, germanium, lead, indium, gallium, zinc, and mixtures thereof. Catalytically effective amounts of such metal modifiers may be incorporated into the catalyst by any means known in the art to effect a homogeneous or stratified distribution.

Further details of the preparation and regeneration of a preferred catalyst composite useful in the present invention are disclosed in U.S. Pat. No. 6,355,853 B1, incorporated herein by reference thereto.

The foregoing description and following examples are presented only to illustrate certain specific embodiments of the invention, and should not be construed to limit the scope of the invention as set forth in the claims. There are many possible other variations, as those of ordinary skill in the art will recognize, which are within the spirit of the invention.

EXAMPLES

Two MFI zeolite samples were formed in solution, recovered by standard means, and washed. The wet sieves were sent to a wet miller and milled with a severity to achieve particle size distributions as follows:

Example 1

Median particle size 1.1 to 1.3 microns (average 1.2 microns)
Mean particle size 1.3 to 1.4 microns (average 1.3 microns)

Example 2

Median particle size 1.3 to 1.7 microns (average 1.5 microns)
Mean particle size 1.2 to 2.4 microns (average 1.8 microns)

Example 3

A silica-bound MFI catalyst was prepared to illustrate the isomerization process of the invention. Ammonia-exchanged MFI-type zeolite having an $Si/Al_2$ ratio of about 38 was blended with Methocel in a muller. Hydrated amorphous silica powder, Ludox AS-40, was added in proportion to effect a final catalyst MFI content of about 67 mass-%. The mixture and sufficient deionized water to effect an extrudable dough having a moisture content of about 40 mass-% was blended thoroughly in the muller. The dough then was extruded through a cylindrical die to form cylindrical extrudates having a diameter of about 1.6 mm. The extrudates then were water washed, air dried, and calcined at a temperature of about 550° C. and then subjected to steaming at a temperature of about 660° C. in an atmosphere of 40% steam in air for 12 hours. The steamed extrudates then were column-washed with ammonium nitrate at 88° C. for 5 hours, then washed with deionized water and dried at 510° C. for about 9 hours. The dried extrudates were metal-impregnated by rolling in a solution of chloroplatinic acid at temperatures of 60-100° C. for 6-7 hours. Upon completion of the impregnation, the composite was dried, oxidized, and reduced to yield a catalyst utilized in the following pilot-plant experiments.

The feedstock used in the experiments comprised $C_8$ aromatics having the following approximate composition in mol-%:

| | |
|---|---|
| Ethylbenzene | 7.5% |
| Para-xylene | <0.5% |
| Meta-xylene | 69% |
| Ortho-xylene | 23% |

Example 4

The $C_8$-aromatics feedstock was isomerized in a pilot plant according to the known art at a hydrogen-to-hydrocarbon ratio of 4, a mass hourly space velocity of 10, and pressures of 0.96, 1.3 and 1.65 MPa. Temperatures were varied to effect ethylbenzene conversions in a range of from about 43% to about 90%. The results are compared with those of the process of the invention in FIGS. 1, 2 and 3.

Example 5

The $C_8$-aromatics feedstock was isomerized in a pilot plant according to the process of the invention at hydrogen-to-hydrocarbon ratios of 0.1 to 0.4, a mass hourly space velocity of 10, and pressure of 390 kPa. Temperatures were varied to effect ethylbenzene conversions in a range of from about 65% to about 83%. The results are compared with those of the known art in FIGS. 1, 2 and 3.

Example 6

FIG. 1 shows the results of the above tests with respect to xylene losses, e.g., by saturation and cracking, plotted against pilot-plant pressure. The results show that pressure has a significant effect on losses, which range from under 1.5% for the process of the invention and the lowest-pressure case of the known art to around 3% at relatively high pressure.

Example 7

Figure 2:
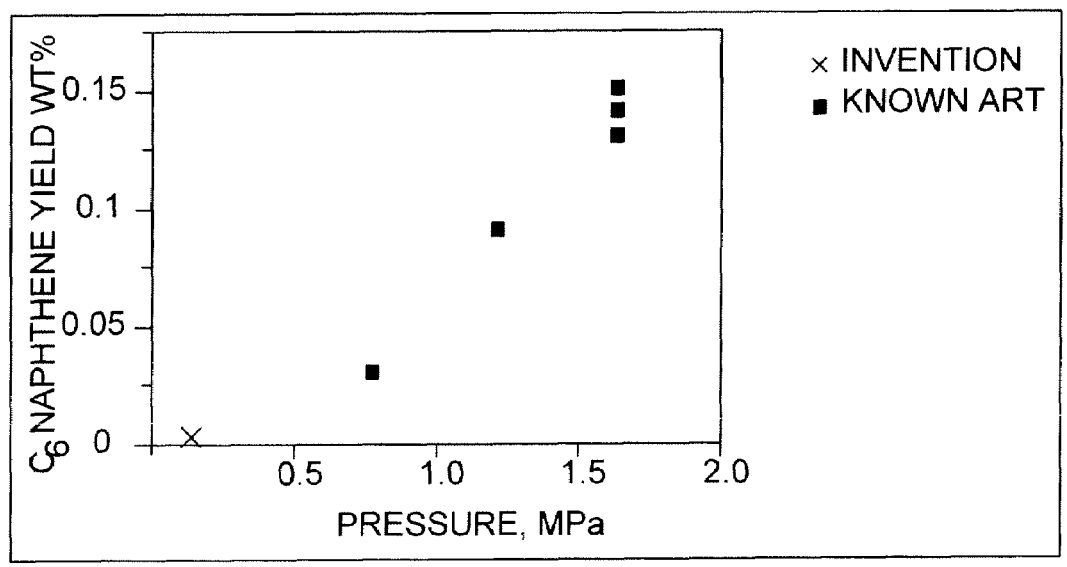
FIG. 2 shows formation of co-boiling naphthene coproducts for the process of the invention compared to a process of the known art.

FIG. 2 shows the results of the above tests with respect to the formation of $C_6$ naphthenes, which not only represent product loss but also contaminate the product, plotted against pilot-plant pressure. The results show that the process of the invention shows a significant advantage over the known art with virtually negligible $C_6$-naphthene formation.

Example 8

Figure 3:
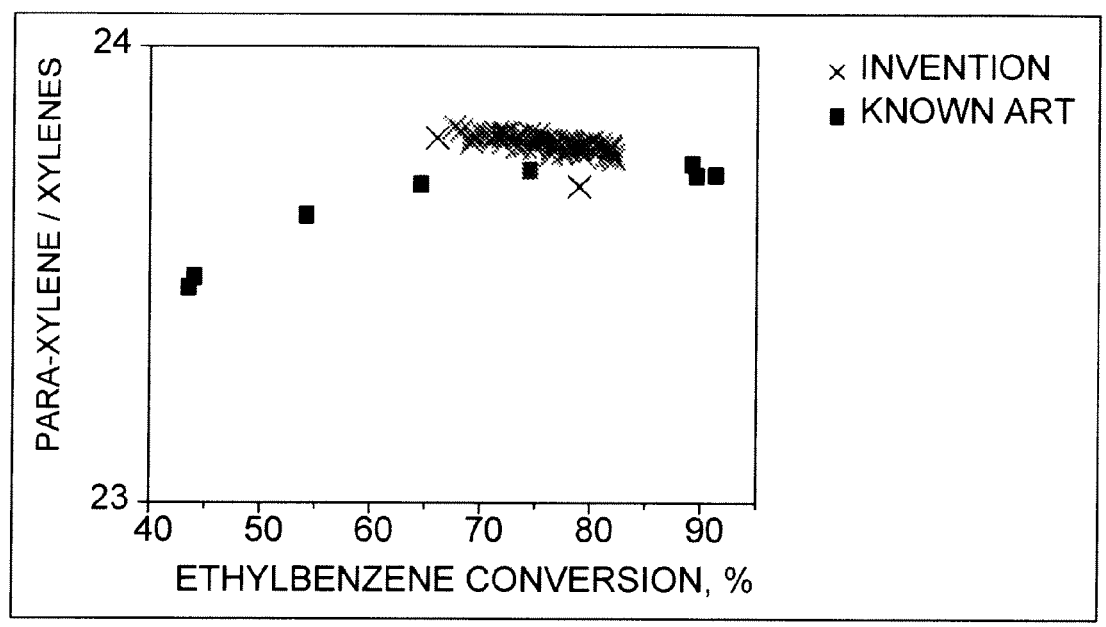
FIG. 3 shows para-xylene/total xylene ratios for the process of the invention compared to a process of the known art.

FIG. 3 shows the results of the above tests with respect to xylene isomerization, represented by the ratio of para-xylene to total xylenes in the product, plotted against ethylbenzene conversion. The results show a slightly higher ratio of para-xylene in the product for the process of the invention over the indicated range of conversion.

Example 9

Test results for three $C_8$-aromatics isomerization cases were developed for commercial capacities with variations in hydrogen ratios in order to assess potential cost savings from utilizing the process of the invention. The assessment was carried out at three different hydrogen-to-hydrocarbon ratios: 0.1 or 0.2, representing the process of the invention; 0.5, representing the known art; and the ratio of the original cases, ranging from 2.4 to 3.3 and also representing the known art.

Hydrogen usage is higher for the recycle cases of the known art, since hydrogen must be purged from the recycle gas to remove hydrocarbons introduced with the feed hydrogen and produced in the isomerization reaction. The hydrogen is valued for this assessment at $0.0135/cubic meter ($NM^3$).

Other principal sources of cost differences are in the recycle-gas compressor, required in processes of the known art but not present in the once-through-hydrogen environment of the process of the invention. Cost differences were assessed based on electric power at $0.06/kilowatt-hour and annual capital charges at 15%/year of differential investment cost.

This assessment does not consider the economic advantages of the invention associated with yield differences as noted in Examples 7-9. The advantages indicated here for the invention thus are conservative.

Example 10

This comparison is based on an isomerization feedstock capacity of 650,000 metric tons/year, with a feedstock composition substantially congruent to that indicated above and a feed hydrogen purity of 92 mol-%. Assessment of costs as described above showed the following principal differences:

| | | Invention | Known Art: Differential Cost | |
|---|---|---|---|---|
| Hydrogen/hydrocarbon | | 0.1 | 0.5 | 2.4 |
| $1000s: | Hydrogen cost | base | 176 | 176 |
| | Power cost | base | 18 | 124 |
| | Capital charge | base | 38 | 182 |
| | Total D cost | base | 232 | 482 |

Example 11

This comparison is based on an isomerization feedstock capacity of 1,750,000 metric tons/year, with a feedstock composition similar to that indicated above and a feed hydrogen purity of 92 mol-%. Assessment of costs as described above showed the following principal differences:

| | | Invention | Known Art: Differential Cost | |
|---|---|---|---|---|
| Hydrogen/hydrocarbon | | 0.1 | 0.5 | 2.4 |
| $1000s: | Hydrogen cost | base | 235 | 235 |
| | Power cost | base | 54 | 483 |
| | Capital charge | base | 73 | 419 |
| | Total D cost | base | 362 | 1137 |

Example 12

This comparison is based on an isomerization feedstock capacity of 1,750,000 metric tons/year, with a feedstock composition similar to that indicated above but at higher ethylbenzene conversion and a feed hydrogen purity of 92 mol-%. Assessment of costs as described above showed the following principal differences:

|  | Invention | Known Art: | Differential Cost |
|---|---|---|---|
| Hydrogen/hydrocarbon | 0.2 | 0.5 | 2.4 |
| $1000s: Hydrogen cost | base | 41 | 41 |
| Power cost | base | 45 | 461 |
| Capital charge | base | 63 | 400 |
| Total D cost | base | 149 | 902 |

The invention claimed is:

1. A process for the isomerization of a non-equilibrium $C_8$-aromatic feedstock comprising contacting the feedstock with a catalyst comprising from about 10 to 99 mass-% of an MFI zeolitic aluminosilicate having a pore diameter of from 5 to 8 angstroms and a median particle size of between about 1.2 and 1.7 microns, from about 200 to 800 mass-ppm on an elemental basis of a platinum metal component, and the balance of a silica binder, wherein the catalyst has a 4.6 torr water capacity between 3 to 5 mass-%, in an isomerization zone at isomerization conditions comprising a temperature of from about 320° C. to 500° C., a pressure of less than 500 kPa, and a mass hourly space velocity of from about 5 to 50 $hr^1$ in the presence of a critical added amount hydrogen on a once-through basis in a molar ratio relative to the feedstock of from about 0.05 to 0.4 to obtain an isomerized product comprising a higher proportion of para-xylene than in the feedstock.

2. The process of claim 1 wherein the critical added amount of hydrogen is in a molar ratio relative to the feedstock of from about 0.05 to 0.1.

* * * * *